US006453498B1

United States Patent
Wu

(10) Patent No.: US 6,453,498 B1
(45) Date of Patent: Sep. 24, 2002

(54) ELECTRIC TOOTHBRUSH

(75) Inventor: Ka Shing Wu, Hong Kong (HK)

(73) Assignee: Addway Engineering Limited, Hong Kong (HK)

( * ) Notice: Subject to any disclaimer, the term of this patent is extended or adjusted under 35 U.S.C. 154(b) by 49 days.

(21) Appl. No.: 09/625,532

(22) Filed: Jul. 26, 2000

(30) Foreign Application Priority Data

Jul. 30, 1999 (GB) .............................................. 9918081

(51) Int. Cl.[7] ........................... A61C 17/34; A46B 13/02
(52) U.S. Cl. ........................... 15/22.1; 15/22.2; 15/22.4
(58) Field of Search .............................. 15/22.1, 167.1, 15/22.2, 22.4, 28; 433/114, 103, 118, 122

(56) References Cited

U.S. PATENT DOCUMENTS

| 2,372,731 A | * | 4/1945 | Nalbach et al. ............... 15/22.1 |
| 2,379,049 A | * | 6/1945 | Tompkins .................... 15/22.1 |
| 2,648,787 A | * | 8/1953 | Smithson, Jr. ................ 15/22.1 |
| 3,159,859 A | * | 12/1964 | Rasmussen .................. 15/22.1 |
| 3,168,834 A | * | 2/1965 | Smithson ..................... 15/22.1 |
| 3,270,360 A | * | 9/1966 | Kropp ........................ 15/22.1 |
| 3,379,906 A | * | 4/1968 | Spohr ........................ 15/22.1 |
| 3,535,726 A | * | 10/1970 | Sawyer ....................... 15/22.1 |
| 3,546,501 A | * | 12/1970 | Kircher ....................... 310/50 |
| 3,699,952 A | * | 10/1972 | Waters et al. ................ 15/22.1 |
| 4,175,299 A | | 11/1979 | Teague, Jr. et al. .......... 15/22.1 |
| 5,448,792 A | * | 9/1995 | Wiedemann et al. ........ 15/22.1 |

FOREIGN PATENT DOCUMENTS

| GB | 1488628 | 10/1977 |
| GB | 1580130 | 11/1980 |

* cited by examiner

Primary Examiner—Gary K. Graham
(74) Attorney, Agent, or Firm—Jackson Walker L.L.P.

(57) ABSTRACT

An electric toothbrush has a housing incorporating a motor with a drive shaft rotatable about a longitudinal axis A. A shank extends beyond the housing and is integrally formed with a brush head at its remote end. The shank is pivotably supported intermediate its length in an end wall of the housing. An eccentric cam mounted to the shaft cooperates with a cup on a near end of the shank to form a mechanical coupling. When the shaft rotates both the near end and the brush head moves through a circular path.

4 Claims, 1 Drawing Sheet

ELECTRIC TOOTHBRUSH

BACKGROUND OF THE INVENTION

1. Field of the Invention

The invention relates to electric toothbrushes.

2. Description of Prior Art

Electric toothbrushes are well-known and generally comprise a handle incorporating a motor and a shank that fits to the housing and has a brush head at its remote end. The motor is arranged to move bristles held in the brush head to cause the bristles to rotate or vibrate in some cases by vibrating the shank relative to the housing. In this way a more efficient brushing and cleaning action is achieved than simply manually moving the bristles over the surfaces of teeth and gums.

Electrical toothbrushes also have switches to turn the motor ON and OFF and in some case to enable different motor speeds to be selected. Normally, the present day toothbrushes have compartments for a battery, which may be a re-chargeable battery. The brush head may detachable from the shank, for cleaning or replacement. These are all features well-known in the art and so will not be further described in the specification. The present invention is more particularly concerned with the manner of driving a brush head, which so far is often complex, and/or comparatively expensive to make, and/or prone to failure.

SUMMARY OF THE INVENTION

It is an object of the invention to overcome or at least reduce these problems.

According to the invention there is provided an electric toothbrush comprising a housing incorporating an electric motor having a drive shaft that rotates about a longitudinal axis of the housing, a shank extending beyond one end of the housing generally in line with the longitudinal axis that supports a brush head at its remote end, in which the shank is pivotably supported intermediate its length adjacent the one end of the housing, and including a mechanical coupling between the drive shaft and a near end of the shank arranged to cause both the near end and the brush head to move through a circular path as the drive shaft rotates.

The mechanical coupling may comprise an eccentric cam mounted to one of the drive shaft and the near end of the shank and a cup that fits over and engages sides of the cam on the other of the drive shaft and the near end of the shank.

The eccentric cam may have a peripheral continuous channel that extends axially with respect to the longitudinal axis and the cup has a finger that engages in the channel so that when the drive shaft rotates the cup (and the shank) is urged backwards and forwards along the longitudinal axis.

The shank may be held to pivot by the sides of an aperture formed in a wall of one end of the housing.

A resilient sealing member may be included that fits around the shank and to the said wall.

The general "toothbrush arrangement" may also be used for skin care products such as brushes or rubbing pads.

BRIEF DESCRIPTION OF THE DRAWINGS

Electric toothbrushes according to the invention will now be described by way of example with reference to the accompanying Schematic drawings in which.

DESCRIPTION OF THE PREFERRED EMBODIMENT

Figure 1:
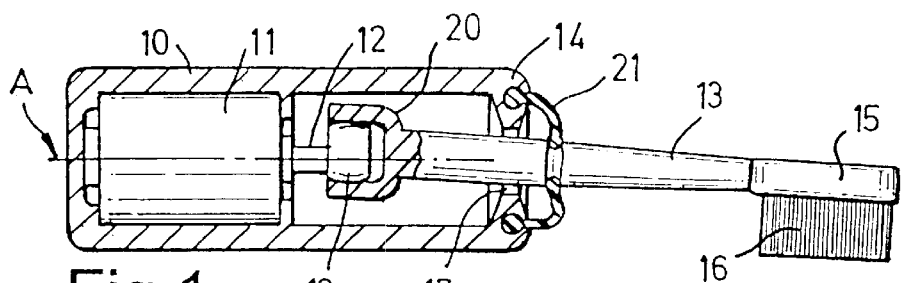
FIG. 1 is a sectional bottom view of one toothbrush.
Figure 2:
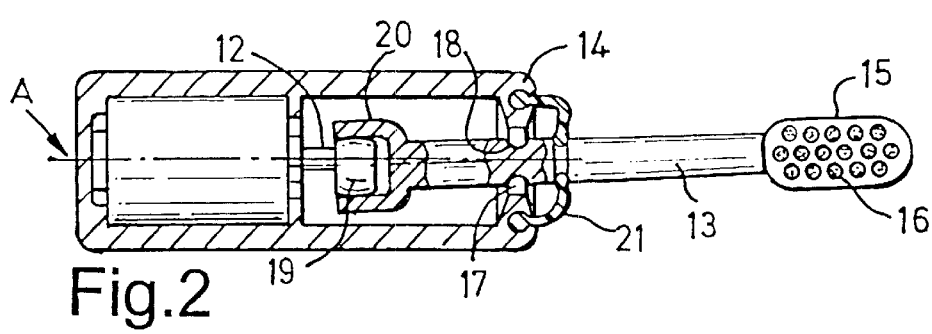
FIG. 2 is a sectional side view of the toothbrush.

Referring to the drawings, in FIGS. 1 and 2 the toothbrush comprises a housing 10 incorporating an electric motor 11 having a drive shaft 12 rotatable about a longitudinal axis A. A shank 13 extends generally in line with the longitudinal axis beyond one end 14 of the housing 10. The shank 13 is integrally formed with a brush head 15 to which a number of bristle tufts 16 are mounted. A single tuft may be supported in the brush head and used for cleaning teeth and gums. Single tufts are known and often referred to an "inter dental cleaners".) The shaft 13 is pivotally supported intermediate its length by an aperture formed in the end 14 of the housing. A circular washer 17 mounted in the aperture fits into a peripheral groove 18 formed in the shank 13.

The drive shaft 12 and a near end of the shank 13 are mechanically coupled so that when the motor 11 is running both the near end and the brush head describes a circle. This is achieved by an eccentric cam 19 mounted to the drive shaft 12 that couples with a cup 20 on the near end of the shank. The cup 20 slidingly fits over the cam 19 and bears against the cam surface in use.

A resilient sealing member 21 fits snugly into a groove 22 formed in the shank 13 and to the end 14 of the housing.

It will be appreciated that the mechanical coupling may comprise an "eccentric" cup 19 on the drive shaft 12 and a cam that runs inside the cup fitted on the near end of the shank 13. Such a coupling will also cause the brush head to describe a circle when the shaft 12 is rotated.

Figure 3:
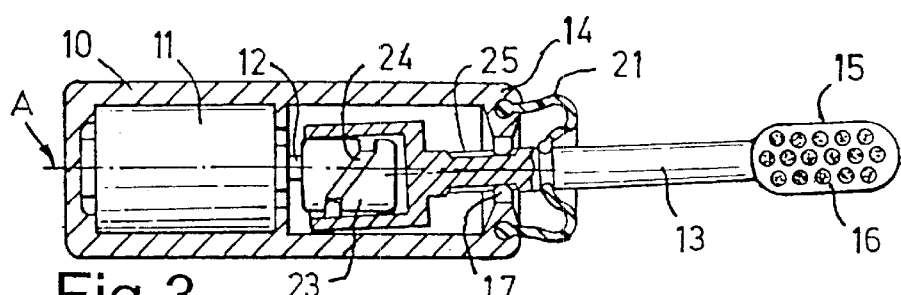
FIG. 3 is a sectional bottom view of another toothbrush.
Figure 4:
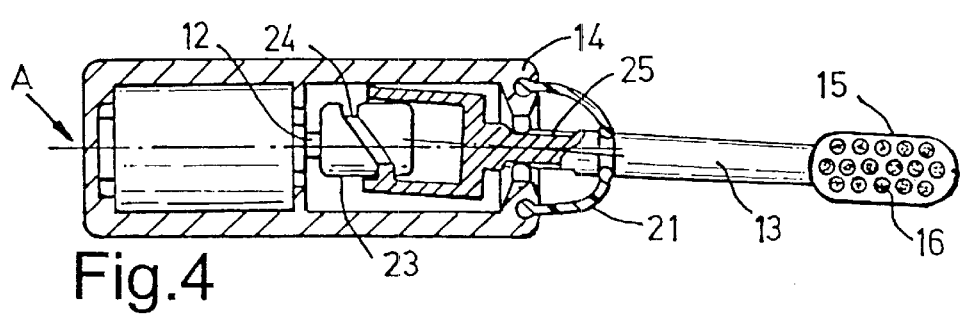
FIG. 4 is a sectional bottom view of the other toothbrush in a different configuration.
Figure 5:
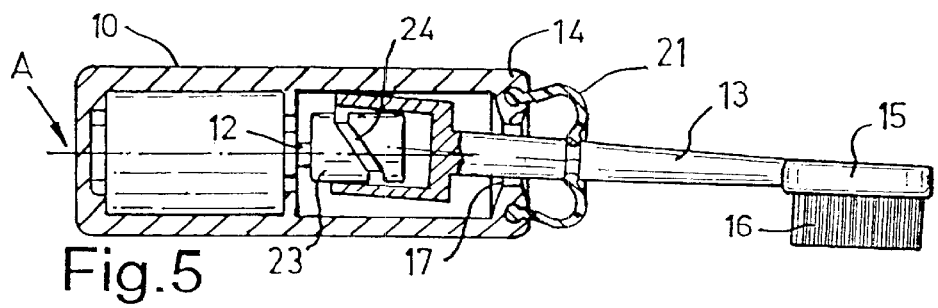
FIG. 5 is a sectional side view of the other toothbrush.

In FIGS. 3, 4 and 5 a similar electric toothbrush is shown except a different mechanical coupling between the drive shaft and the near end of the shank is provided. An eccentric cam 23 is formed with a continuous slot 24. The slot 24 extends in an axial direction with respect to the longitudinal axis A. Thus, when the drive shaft 12 rotates the brush head 15 describes a circle as in FIGS. 1 and 2, and also moves backwards and forwards along the longitudinal axis. Thus, the brush head 15 is moved through a three-dimensional elliptical path as the drive shaft 12 rotates.

The FIGS. 3, 4 and 5 show three different configurations each represents the head in respective positions along the elliptical path. In order to allow the shank to pivot and to slide as required, a short neck or groove 25 is formed that fits snugly into and is supported by the circular washer 17.

It will be noted in FIGS. 1 and 2 a section 26 of the shank is shown in cross-hatching. The shank 13 is normally formed of relatively rigid plastics material and the section 26 is made of relatively flexible material. This allows the shaft adjacent the cup 20 to flex more and such that, if the brush head 15 is held stationary when the motor 11 is turned ON, the motor can start to drive the cam 19 as required. If the shank cannot flex sufficiently for this condition, the motor may stall when initially switched ON.

It will be appreciated that the required or preferred differential flexibility may be provided in other manners such as by narrowing the diameter of a section of the shank. It will also be appreciated that the "flexible" section 26 may be placed in the shank at other positions along its length, that is, on either side of its pivotable support.

Hand-held skin care appliances may also be provided using the "toothbrush arrangement" described herein. In such appliances the described bristles are replaced with softer bristles or a pad that can be pressed against the skin and vibrated/oscillated to clean and stimulate the surface of the skin as required.

I claim:

1. An electric toothbrush comprising:
   a housing incorporating an electric motor having a drive shaft that rotates about a longitudinal axis of the housing;
   a shank extending beyond one end of the housing generally in line with the longitudinal axis that supports a brush head at its remote end, the shank being pivotably supported intermediate its length adjacent the one end of the housing; and
   a mechanical coupling between the drive shaft and a near end of the shank arranged to cause both the near end and the brush head to move through a circular path as the drive shaft rotates, the mechanical coupling further comprising an eccentric cam mounted to the drive shaft and a cup that fits over and engages sides of the cam on the drive shaft, the cup mounted on the near end of the shank, the eccentric cam having a peripheral continuous channel that extends axially with respect to the longitudinal axis and the cup has a finger that engages in the channel so that when the drive shaft rotates the cup is urged backwards and forwards along the longitudinal axis.

2. An electric toothbrush according to claim 1, in which the shank is held to pivot by sides of an aperture formed in a wall of said one end of the housing.

3. An electric toothbrush according to claim 2, including a resilient sealing member that fits around the shank and to the said wall.

4. An electric toothbrush according to claim 1, in which a relatively flexible section of the shank is provided in the shank at one side of its pivotable axis.

* * * * *